(12) United States Patent
Koller

(10) Patent No.: US 6,207,833 B1
(45) Date of Patent: Mar. 27, 2001

(54) METHOD FOR THE PREPARATION OF (2-QUINOLYTHIO)ACETIC ACID AND ITS HYDROCHLORIDE

(75) Inventor: Herbert Koller, Vienna (AT)

(73) Assignee: Loba Feinchemie AG, Fischamend (AU)

( * ) Notice: Subject to any disclaimer, the term of this patent is extended or adjusted under 35 U.S.C. 154(b) by 0 days.

(21) Appl. No.: 09/599,601

(22) Filed: Jun. 23, 2000

(30) Foreign Application Priority Data

Jun. 23, 1999 (AU) .................................... 1102/99

(51) Int. Cl.[7] .................................. C07D 215/16
(52) U.S. Cl. ................................................. 546/157
(58) Field of Search ............................... 546/157

(56) References Cited

U.S. PATENT DOCUMENTS 5,658,751 * 8/1997 Koller et al. .

FOREIGN PATENT DOCUMENTS 0631176   12/1994   (EP) .

OTHER PUBLICATIONS

Duffin et al., "Anhydro–compounds from Nitrogen–containing Derivatives of Thioglycollic Acid. Part 1. Pyridine and Quinoline Compounds.", J. Chem. Soc, 1951, pp. 734–739.

* cited by examiner

*Primary Examiner*—John Kight
*Assistant Examiner*—Binta Robinson
(74) *Attorney, Agent, or Firm*—Wenderoth, Lind & Ponack, L.L.P.

(57) ABSTRACT

The invention relates to a single stage method for preparing 2-(quinolylthio)acetic acid and its salts by reacting 2-chloroquinoline and mercaptoacetic acid

10 Claims, No Drawings

METHOD FOR THE PREPARATION OF (2-QUINOLYTHIO)ACETIC ACID AND ITS HYDROCHLORIDE

The invention relates to a method for preparing (2-quinolylthio)acetic acid.

(2-quinolylthio)acetic acid and 2-(quinolylthio)acetic acid hydrochloride are important intermediates for the preparation of stabilizers in photothermographic materials, which are disclosed for example in EP 0 631 176.

Methods for the production of 2-(quinolylthio)acetic acid are known in prior art.

For example G. F. Duffin, J. D. Kendall, J.Chem.Soc, 1951, pp. 734 ff disclose a process for the preparation of 2-(quinolylthio)acetic acid by reacting quinoline-2-thiol with thioacetic acid. Quinoline-2-thiol is obtained by reacting 2-chloroquinoline with thiourea.

The present invention provides a single stage method for the production of 2-(quinolylthio)acetic acid by reacting 2-chloroquinoline with mercaptoacetic acid; the desired 2-(quinolylthio)acetic acid is obtained with high purity and yield.

Therefore the object of the invention is a method for the production of 2-(quinolylthio)acetic acid of formula I

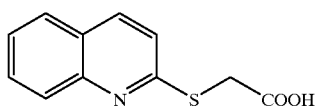

(I)

and its salts, comprising reacting 2-chloroquinoline of formula II

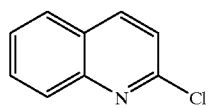

(II)

with mercaptoacetic acid in aqueous medium and, if desired, converting the resulting salt into the free acid or the resulting acid into its salt.

The method of the invention provides high yields and high purity which is necessary for the use of the product for example in the process described in EP 0 631 176.

2-chloroquinoline is melted and further reacted with mercaptoacetic acid in aqueous medium. The reaction mixture is heated, cooled and the product I is precipitated.

The reaction may be carried out in alkaline or acidic medium.

At first 2-chloroquinoline is melted at a temperature of about 60 to 70° C.

If the reaction is carried out in an alkaline medium an inorganic base, for example NaOH, KOH etc. and if desired tetrabutylammoniumiodide as phase-transfer catalyst is added.

Then mercaptoacetic acid is added, if desired in aqueous alkaline solution. The reaction mixture is heated to reflux temperature. After the reaction is finished the reaction mixture is cooled to room temperature and further, if desired, washed with an inert organic solvent, such as ethers, like t-butylmethylether, or ethylacetate or toluene or benzene etc. The aqueous phase is then acidified by adding an inorganic acid, such as HCl, the product is precipitated as its hydrochloride. Precipitation is done in acidic medium at a pH of about <1. The resulting precipitate is washed, for example with distilled water and dried.

The reaction may be carried out at low temperatures. The melted 2-chloroquinoline is taken up in aqueous medium, e.g. distilled water, and mercaptoacetic acid is added at a temperature of 35 to 65° C., preferably 45–50° C. After the reaction is finished, the reaction mixture is cooled, preferably to a temperature of 40–60° C. and the pH of the reaction mixture is adjusted to 8–11, preferably to 9–10 by adding a base, for example NaOH, KOH or the like. Then the reaction mixture is cooled to room temperature. Washing and precipitation is done as indicated above.

If 2-(quinolylthio)acetic acid is obtained by adding HCl in the form of its hydrochloride, the free acid may be isolated by solving the hydrochloride for example in an aqueous solution of sodiumhydrogencarbonate or sodiumcarbonate or the like, follwed by further precipitation in acidic medium, for example at a pH of about 3–4.

If the reaction is carried out in acidic medium, the molten 2-chloroquinoline is taken up in an aqueous medium, for example distilled water and an inorganic acid, for example HCl conc. is added. Further mercaptoacetic acid is added and the reaction mixture is heated to a temperature of 45° C. to reflux temperature of the reaction mixture. After the reaction is finished, the reaction mixture is cooled to room temperature to 0° C. and if desired is diluted with an inert water mixable solvent, for example acetone.

Further the pH may be adjusted to about 8–11, preferably 9–10 by adding an inorganic base; isolation of the free acid is done as indicated above.

Reaction time is dependant on the reaction temperature and is usually about 10 min to 24 h, preferably 30 min to 12 h. The reaction is monitored by conventional methods like thin layer chromatography and the like.

The hydrochloride obtained by the above mentioned method as well as the free acid obtained by the above mentioned method may be used as intermediate in the process described in EP 0 631 176. In this case the sodium salt of 2-(quinolyl)thio-acetic acid is formed by adding two equivalents of the appropriate base, for example sodiumhydroxide. Further process steps are described in EP-0 631 176.

The sodium salt of 2-(quinolylthio)acetic acid is reacted with bromine and sodiumhydroxide at a temperature below 30° C., the precipitate is siphoned and dried. If desired the precipitate is recrystallized.

EXAMPLE 1

150,0 g (0,917 mol) 2-chloroquinoline were melted at a temperature of 60–70° C. and 400 ml NaOH 10% (ca. 1,2 equiv.) and 1,5 g (0,004 equiv.) tetrabutylammoniumiodide were added. Further a solution of 105,6 g (1,25 equiv.) mercaptoacetic acid in 450 ml NaOH 10% (ca.1,2 equiv.) was added at 70–80° C. within 30 min. The reaction mixture was refluxed for 13 hours, cooled to about 25° C. and washed with 200 ml t-butylmethylether three times.

The aqueous phase was then adjusted to a pH<1 by adding HCl conc. at a temperature of max. 5° C. The hydrochloride precipitated and was washed with 250 ml water twice after siphoning. The wet filtration residue was suspended in 800 ml water and solved by adding 160 g sodium hydrogen carbonate.

2-quinolylthioacetic acid was precipitated by acidifying the solution to a pH of 3–4 with HCl, siphoned and the filtration residue was washed twice with 200 ml water.

After drying at a temperature of about 50–60° C. in vacuum the yield was 158,9 g (79% th.), 99,5% purity (HPLC)

Fp.: 90,5–91,9° C.

EXAMPLE 2

150,0 g (0,917 mol) 2-chloroquinoline were melted at a temperature of 60–70° C. and 530 ml NaOH 15% (ca. 2,5 equiv.) and 1,5 g (0,004 equiv.) tetrabutylammoniumiodide were added. The mixture was heated to reflux temperature. 105,6 g (1,25 equiv.) mercaptoacetic acid were added within 5 min and the reaction mixture was refluxed for 13,5 hours and then diluted with 250 ml water and cooled to about 25° C. and further washed with 200 ml t-butylmethylether three times.

The aqueous phase was then adjusted to a pH<1 by adding HCl conc. at a temperature of max. 5° C. The hydrochloride precipitated and was washed with 250 ml water twice after siphoning. After drying at a temperature of about 50–60° C. in vacuum the yield was 193,4 g (83% th.), 97,0% purity (HPLC)

EXAMPLE 3

250,0 g (1,528 mol) 2-chloroquinoline were melted at a temperature of 60–70° C. and 1340 ml NaOH 10% (ca. 2,4 equiv.) and 2,5 g (0,004 equiv.) tetrabutylammoniumiodide were added. 176,0 g (1,25 equiv.) mercaptoacetic acid were added within 5 min at a temperature of 70–80° C., the reaction mixture was refluxed for 13 hours. After cooling to 25° C. the mixture was washed with 300 ml t-butylmethylether three times.

The aqueous phase was then adjusted to a pH of about 3–4 by adding HCl conc. at a temperature of max. 5° C. The producted washed with 250 ml water twice after siphoning. After drying at a temperature of about 50–60° C. in vacuum the yield was 316,3 g (94% th.), 99,3% purity (HPLC)

Fp.: 92,3–96,6° C.

EXAMPLE 4

25 g (0,153 mol) 2-chloroquinoline were melted at a temperature of 60–70° C. After adding 140 ml water and 0,25 g (0,004 equiv.) tetrabutylammoniumiodide 17,6 g (1,25 equiv.) mercaptoacetic acid were added within 5 min and the reaction mixture was refluxed for 1 hour. After cooling to 20° C. the pH was adjusted to 8–9 by adding NaOH (50%). Then the pH was adjusted to 3–4 at a temperature of max. 5° C. The product was washed with 50 ml water twice after siphoning. After drying at a temperature of about 50–60° C. in vacuum the yield was 30,1 g (90%), 80,2% purity (HPLC).

Fp.: 79,8–81,5° C.

EXAMPLE 5

92,0 g (0,562 mol) 2-chloroquinoline were melted at a temperature of 60–70° C. After adding 350 ml water 64,8 g (1,25 equiv.) mercaptoacetic acid were added within 5 min and the reaction mixture was refluxed for 50 min and then and cooled to about 50° C. The pH was adjusted to 8–9 by adding NaOH (50%). The reaction mixture was then cooled to 20–25° C. and washed with 150 ml ethylacetate three times. The aqueous phase was acidified to a pH of 3–4 by adding HCl conc. at a temperature of max. 5° C. The product was siphoned and washed with 150 ml water twice. After drying at a temperature of about 50–60° C. in vacuum the yield was 105,2 g (85% th.), 92,3% purity (HPLC).

Fp.: 85,8–87,5° C.

EXAMPLE 6

200,0 g (1,222 mol) 2-chloroquinoline were melted at a temperature of 60–70° C. After adding 750 ml water 124,3 g (1,10 equiv.) mercaptoacetic acid were added within 20 min at a temperature of 80–85° C. and the reaction mixture was stirred for 1 h at a temperature of 80–85° C. and then and cooled to about 40° C. The pH was adjusted to 9–10 by adding NaOH (32%). The reaction mixture was then cooled to 20–25° C. and washed with 250 ml toluene three times and diluted with 300 ml water. The aqueous phase was acidified to a pH of 3–4 by adding HCl conc. at a temperature of max. 5° C. The product was siphoned and washed with 250 ml water three times. After drying at a temperature of about 50–60° C. in vacuum the yield was 232,9 g (87% th.), 91,8% purity (HPLC).

Fp.: 86,9–89,3° C.

EXAMPLE 7

100,0 g (0,611 mol) 2-chloroquinoline were melted at a temperature of 60–70° C. After adding 500 ml water 70,4 g (1,25 equiv.) mercaptoacetic acid were added within 5 min at a temperature of 45–50° C. and the reaction mixture was stirred at this temperature for 13 hours. The pH was adjusted to 9–10 by adding NaOH (32%). The reaction mixture was then cooled to 20–25° C. and washed with 150 ml toluene three times. After diluting the reaction mixture with 350 ml water, the aqueous phase was acidified to a pH of 3–4 by adding HCl conc. at a temperature of max. 5° C. The product was siphoned and washed with 250 ml water three times. After drying at a temperature of about 50–60° C. in vacuum the yield was 113,2 g (85% th.), 98,2% purity (HPLC).

Fp.: 89,5–91° C.

EXAMPLE 8

100,0 g (0,611 mol) 2-chloroquinoline were melted at a temperature of 60–70° C. After adding 500 ml water 70,4 g (1,25 equiv.) mercaptoacetic acid were added within 5 min at a temperature of 95° C. and the reaction mixture was refluxed at a temperature of 100–105° C. for 20 min and then cooled to 40–45° C. The pH was adjusted to 9–10 by adding NaOH (32%). The reaction mixture was then cooled to 20–25° C. and washed with 150 ml toluene three times. After diluting the reaction mixture with 350 ml water, the aqueous phase was acidified to a pH of 3–4 by adding HCl conc. at a temperature of max. 5° C. The product was siphoned and washed with 250 ml water three times. After drying at a temperature of about 50–60° C. in vacuum the yield was 106,4 g (79% th.), 91,7% purity (HPLC).

Fp.: 86,7–89,3° C.

EXAMPLE 9

100,0 g (0,611 mol) 2-chloroquinoline were melted at a temperature of 60–70° C. and 500 ml water and 51 ml (1,00 equiv.) HCl conc. were added. Further 70,4 g (1,25 equiv.) mercaptoacetic acid were added within 5 min at reflux temperature and the reaction mixture was refluxed for 20 min. After cooling to a temperature of 40–45° C. the pH was adjusted to 9–10 by adding NaOH (32%). The reaction mixture was then cooled to 20–25° C. and washed with 150 ml toluene three times and further diluted with 350 ml water. The aqueous phase was acidified to a pH of 3–4 by adding HCl conc. at a temperature of max. 5° C. The product was siphoned and washed with 250 ml water three times. After drying at a temperature of about 50–60° C. in vacuum the yield was 111,8 g (83%), 84,5% purity (HPLC).

Fp.: 85,5–87,3° C.

EXAMPLE 10

100,0 g (0,611 mol) 2-chloroquinoline were melted at a temperature of 60–70° C. and 500 ml water and 101 ml (2,00 equiv.) HCl conc. were added. Further 70,4 g (1,25 equiv.) mercaptoacetic acid were added within 5 min at reflux temperature and the reaction mixture was refluxed for 30 min. After cooling to a temperature of 0–5° C. the reaction mixture was diluted with 100 ml acetone and the hydrochloride was siphoned and washed twice with 100 ml acetone and twic with 100 ml water. The wet residue was suspended in 500 ml water, pH was adjusted to 9–10 by adding NaOH (32%). The mixture was cooled to 20–25° C. and washed with 200 ml toluene three times. The aqueous phase was acidified to a pH of 3–4 by adding HCl conc. at a temperature of max. 5° C. The product was siphoned and washed with 250 ml water three times.

After drying at a temperature of about 50–60° C. in vacuum the yield was 106,0 g (79%), 80,9% purity (HPLC).

Fp.: 79,3–80,3° C.

EXAMPLE 11

100,0 g (0,611 mol) 2-chloroquinoline were melted at a temperature of 60–70° C. and 400 ml water and 101 ml (2,00 equiv.) HCl conc. were added. Further 70,4 g (1,25 equiv.) mercaptoacetic acid were added within 5 min at 70° C., the reaction mixture was stirred at 65–70° C. for 6 hours. After cooling to a temperature of 0—5° C. the reaction mixture was stirred at 0–5° C. for 30 min. The hydrochloride was siphoned and washed with 100 ml water twice.

After drying at a temperature of about 50–60° C. in vacuum the yield was 142,6 g (91%), 83,5% purity (HPLC).

Fp.: 206,6–208,6° C.

What is claimed is:

1. Method for the production of 2-(quinolylthio)acetic acid of formula I

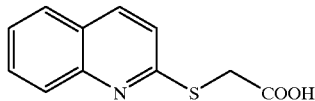

(I)

and its salts, comprising reacting 2-chloroquinoline of formula II

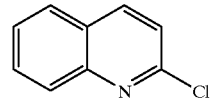

(II)

with mercaptoacetic acid in aqueous medium and, if desired, converting the resulting salt into the free acid or the resulting acid into its salt.

2. Method according to claim 1 wherein the reaction is carried out in alkaline aqueous medium.

3. Method according to claim 2, wherein the reaction is carried out in the presence of NaOH at a pH of 9–10.

4. Method according to claim 2, wherein the pH is adjusted to 9–10 after reacting 2-chloroquinoline and mercaptoacetic acid.

5. Method according to claim 1 wherein the reaction is carried out in the presence of tetrabutylammoniumchloride.

6. Method according to claim 1, wherein the reaction is carried out in acidic aqueous medium.

7. Method according to claim 6 wherein the reaction is carried out in the presence of HCl.

8. Method according to claim 1, wherein the reaction is carried out at a temperature 35° C. to reflux temperature of the reaction mixture.

9. Method according to claim 1 wherein the compound of formula I is 2-(quinolylthio)acetic acid hydrochloride.

10. Method according to claim 1 wherein the compound of formula I is 2-(quinolylthio)acetic acid.

* * * * *